United States Patent [19]

Kratzer et al.

[11] Patent Number: 5,460,779
[45] Date of Patent: Oct. 24, 1995

[54] DEVICE FOR THE AUTOMATIC EXAMINATION OF BLOOD SAMPLES

[75] Inventors: Michael Kratzer, Munich; Volker F. von der Goltz, Seeon, both of Germany

[73] Assignee: Dade International Inc., Deerfield, Ill.

[21] Appl. No.: 430,140

[22] Filed: Apr. 26, 1994

Related U.S. Application Data

[63] Continuation of Ser. No. 889,329, May 28, 1992, abandoned.

[30] Foreign Application Priority Data

May 28, 1991 [DE] Germany .................... 41 17 482.8
Mar. 26, 1992 [DE] Germany .................... 42 09 871.8

[51] Int. Cl.$^6$ ..................... G01N 33/49; G01N 35/02
[52] U.S. Cl. ..................... 422/73; 422/58; 422/63; 422/66; 422/69; 436/48; 436/69; 73/64.41
[58] Field of Search ..................... 422/63, 64, 65, 422/66, 67, 58, 73, 69, 68.1; 436/47, 49, 69; 73/64.41, 64.43

[56] References Cited

U.S. PATENT DOCUMENTS

| | | | |
|---|---|---|---|
| 3,440,866 | 4/1969 | Ness et al. | 73/64.43 |
| 3,486,859 | 12/1969 | Greiner et al. | 422/73 X |
| 3,526,480 | 9/1970 | Imol et al. | 422/66 |
| 3,650,698 | 3/1972 | Adler | 73/64.43 X |
| 3,720,097 | 3/1973 | Kron | 73/54.04 |
| 3,900,290 | 8/1975 | Hornstra | 73/64.41 X |
| 3,991,728 | 10/1995 | Fixot | 73/54.04 |
| 4,071,315 | 1/1978 | Caateau | 422/66 X |
| 4,142,863 | 3/1979 | Covington et al. | 422/63 |
| 4,150,089 | 4/1979 | Linet | 422/102 |
| 4,201,222 | 5/1980 | Haase | 128/634 |
| 4,260,581 | 4/1981 | Sakurada | 422/65 |
| 4,313,735 | 2/1982 | Yamashita et al. | 436/47 |
| 4,395,493 | 7/1983 | Zahniser et al. | 422/66 X |
| 4,463,616 | 8/1984 | Blecher | 73/864.11 |
| 4,528,158 | 7/1985 | Gilles et al. | 436/49 X |
| 4,528,159 | 7/1985 | Liston | 422/65 |
| 4,568,520 | 2/1986 | Ackermann et al. | 422/66 |
| 4,604,894 | 8/1986 | Kratzer et al. | 73/64.1 |
| 4,636,360 | 1/1987 | Sakurada et al. | 422/65 |
| 4,713,219 | 12/1987 | Gerken et al. | 422/102 |
| 4,780,418 | 10/1988 | Kratzer | 73/64.1 X |
| 4,808,381 | 2/1989 | McGregor et al. | 422/10 |
| 4,820,497 | 4/1989 | Howell | 436/49 X |
| 4,857,272 | 8/1989 | Sugaya | 422/65 |
| 4,878,971 | 11/1989 | Tsunekawa et al. | 422/66 X |
| 4,951,512 | 8/1990 | Mazza et al. | 422/64 X |
| 4,962,044 | 10/1990 | Knesel, Jr. et al. | 436/177 |
| 4,999,163 | 3/1991 | Lennon et al. | 422/58 |
| 5,019,243 | 5/1991 | McEwen et al. | 210/94 |
| 5,047,211 | 9/1991 | Sloane, Jr. et al. | 422/73 |
| 5,051,239 | 9/1991 | von der Goltz | 422/73 |

(List continued on next page.)

FOREIGN PATENT DOCUMENTS

| | | |
|---|---|---|
| 0347837 | 12/1989 | European Pat. Off. . |
| 64-37761 | 5/1989 | Japan . |
| 1234044 | 6/1971 | United Kingdom . |
| 2096329 | 10/1982 | United Kingdom . |

OTHER PUBLICATIONS

Scientific Products Catalog—Baxter, 1991–1992, p. 1818.

*Primary Examiner*—Steven Weinstein
*Assistant Examiner*—Milton I. Cano
*Attorney, Agent, or Firm*—Joseph P. Reagen; Tilton, Fallon, Lungmus & Chestnut

[57] ABSTRACT

The invention pertains to a device for the automatic examination of blood samples with one test station, in which blood is taken from a supply vessel and is fed through an aperture in a part held in an aperture holder. At least one test head is provided, to which is fed from a first magazine holder, supply vessels with blood, and from a second magazine holder, aperture holders are fed. After performance of at least one measurement on one aperture holder, the used aperture holder and the used supply vessel are removed from the test head and the test head is cleaned by a cleaning device.

29 Claims, 5 Drawing Sheets

U.S. PATENT DOCUMENTS

| | | | |
|---|---|---|---|
| 5,089,422 | 2/1992 | Brubaker | 436/69 |
| 5,102,624 | 4/1992 | Muralshi | 422/66 X |
| 5,114,860 | 5/1992 | Hayashi | 73/64.41 X |
| 5,211,310 | 5/1993 | Godolphin et al. | 422/100 X |
| 5,215,714 | 6/1993 | Okada et al. | 422/73 X |
| 5,260,872 | 11/1993 | Copeland et al. | 436/69 X |
| 5,296,376 | 3/1994 | Gorog et al. | 73/64.41 X |
| 5,352,413 | 10/1994 | Kratzer et al. | 422/100 X |

DEVICE FOR THE AUTOMATIC EXAMINATION OF BLOOD SAMPLES

This is a continuation, of application Ser. No. 07/889,329, filed on May 28, 1992, now abandoned.

FIELD OF THE INVENTION

The invention pertains to a device for the automatic examination of blood samples.

BACKGROUND OF THE INVENTION

Figures 1, 5, 15:
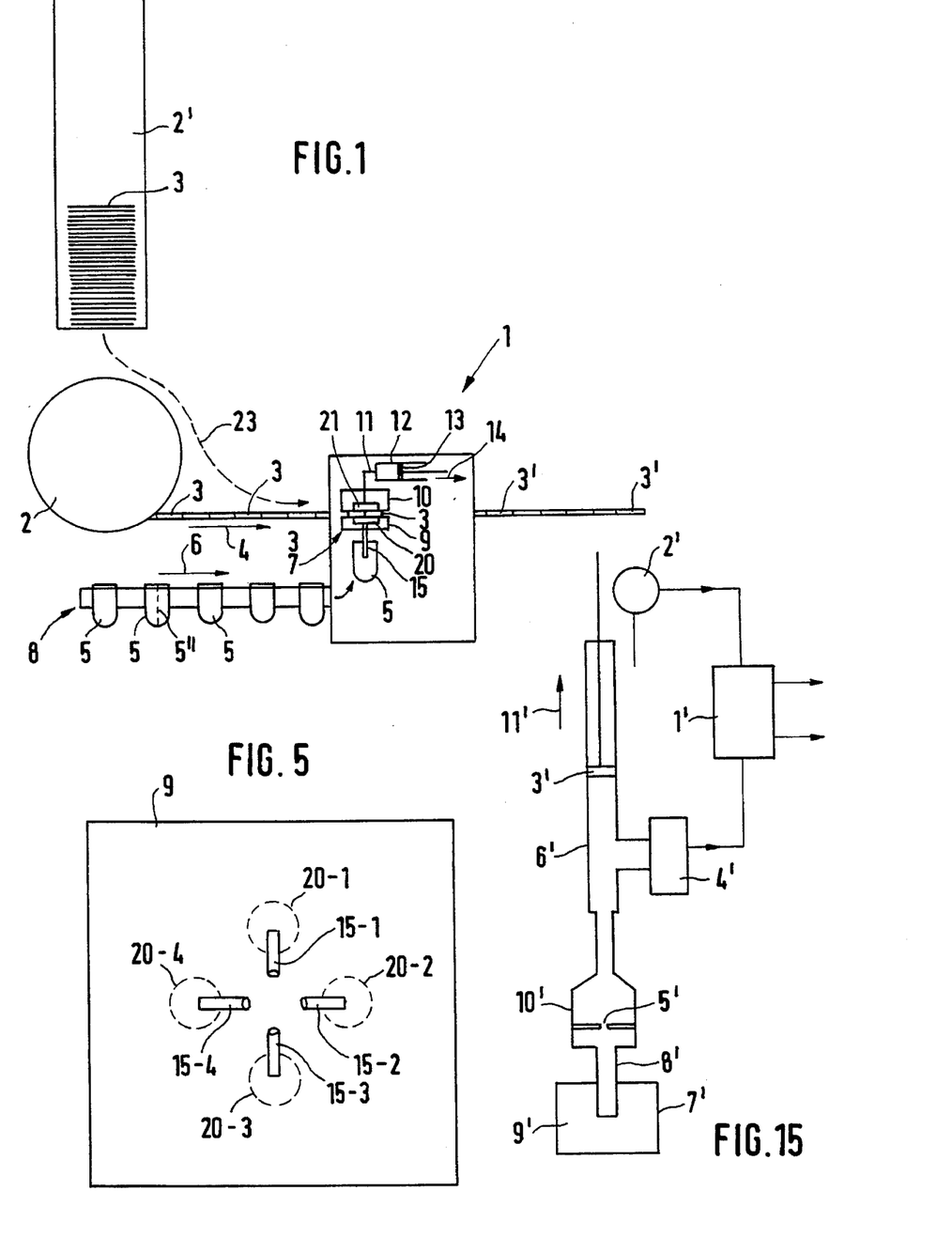
FIG. 1 shows a schematic illustration of the invented device for automatic examination of blood samples.
FIG. 5 shows the view V—V of the capillary holder of the test head of FIG. 2.
FIG. 15 shows an illustration to explain the state of the art.

As is known, the bleeding time in vitro can be measured since according to FIG. 15, blood 9' can be sucked from a supply vessel 7' via an aperture 5' into a cylinder 6', inasmuch as in the cylinder 6', a plunger 3' is moved by a stepping motor 2' in the direction of the arrow 11'. A pressure sensor 4' thereby measures the pressure prevailing in the chamber precircuited to plunger 3'. This pressure will be held to a constant value such that a processor 1' drives the stepping motor 2' as a function of the signal of the pressure sensor 4'. From the movement of the plunger 3' and the diameter of the cylinder 6', the processor 1' computes the volume flow of the blood through the aperture 5'. The aperture 5', whose diameter is at about 150 µm for example, simulates an injured portion of an arteriole. It is located for instance, in a cellulose acetate filter that is coated with collagen. The filter will be saturated with ADP before the measurement. According to the described method, a reproducible measurement of the bleeding time in vitro and of the bleeding volume is possible.

As is known, the aperture 5', that is, the stated filter, is positioned in a housing 10' that can be joined to a capillary 8' that sucks the blood 9' taken from the supply vessel 7' to the aperture 5'.

Now in the described measurement method, one problem consists in the fact that when carrying out a large number of measurements, for example, about 150 measurements per day, a correspondingly large number of aperture holders 10' is needed. These aperture holders 10' that contain the described collagen-coated filters as apertures 5', must be stored in a refrigerator or similar appliance at about 4° C. until they are used. This means that when carrying out measurements on a large scale, the available cooling space needed to prepare the aperture holder 10' will have to be quite large.

The problem of the present invention consists in designing a device for the automatic examination of blood samples where relatively many aperture holders can be positioned in a comparatively small space.

DETAILED DESCRIPTION OF THE INVENTION

This problem will be solved by a device as already described above, that is characterized by the properties stated in the descriptive portion.

The essential advantage of the invented device consists in the fact that it will make it possible to use aperture holders located in a magazine so that very little space is needed for their storage or housing. This will mean that in a given cooling apparatus, very many more aperture holders can be stored and cooled than has been possible heretofore. Thus in addition to a savings in storage space, energy will also be saved.

Now in a preferred design of the invention, the test head and the aperture holder are designed so that in a single measuring operation, several, that is, two times two, investigations can be carried out at the same time; therefore, the savings in space and energy stated above can be greatly increased.

Additional favorable configurations of the invention proceed from the subclaims.

BRIEF DESCRIPTION OF THE DRAWINGS

The invention and its configurations will be explained in detail below in connection with the nonlimiting figures.

DETAILED DESCRIPTION OF THE DRAWINGS

From the fundamental sketch in FIG. 1 it is evident that the present invention has essentially one test station 1 that is fed aperture holders 3 in sequence from a magazine device 2 in the direction of arrow 4.

Furthermore, the blood samples to be examined are also fed to the test station 1, these samples are located in supply vessels 5 and are fed in the direction of arrow 6, in sequence, so that one aperture holder 3 and one supply vessel 5 are always fed at the same time to the test head 7. Now the supply vessel 5 is taken preferably from a magazine 8 and is inverted several times to mix up the blood sample included in it, before its input into the test head 7. Removal of the supply vessel 5 from the magazine 8 and inverting of the supply vessel 5 take place with the assistance of known devices, that will not be described in detail. The test head 7 consists essentially of a capillary holder 9, to which a capillary 15 is mounted, and a head unit 10 that is joined via a line 11 to a cylinder 12, in which a piston 13 is installed. Upon movement of the piston 13 in the cylinder 12 in the direction of the arrow 14, in the line 11 and in the test head 7, an vacuum is produced that causes blood to be pulled from the supply vessel 5 into which the capillary 15 is now immersed, and this blood is sucked through the aperture of the aperture holder 3.

After completion of the individual measurements, the spent aperture holders 3' leave the test station 1 as disposable items.

Figures 2, 3, 4:
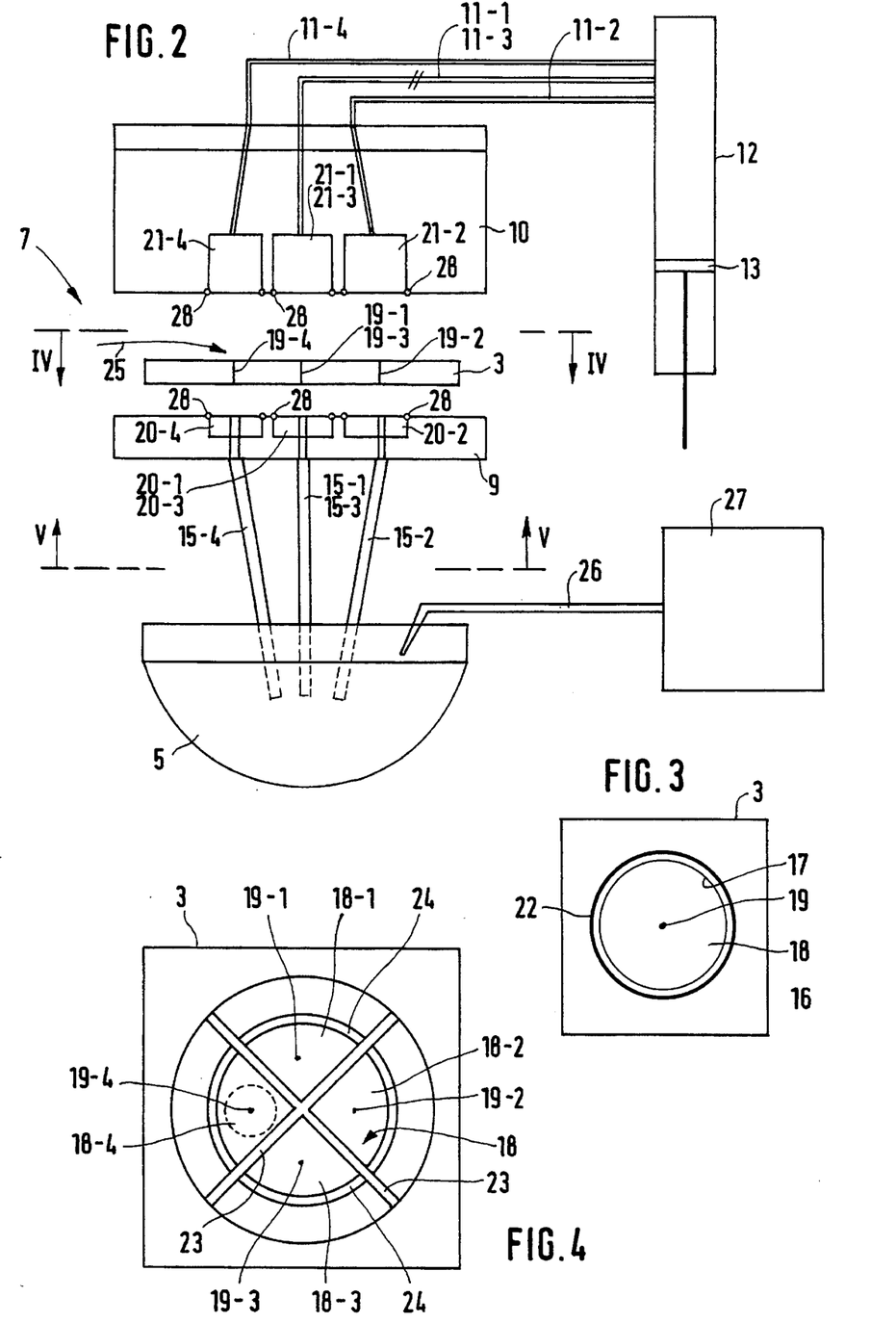
FIG. 2 shows a detailed illustration of the test head of the invented device.
FIG. 3 shows a view of an aperture holder with an aperture.
FIG. 4 shows a view along line IV—IV of FIG. 2 of an aperture holder with several apertures.

In accordance with FIG. 3, an aperture holder 3 has for example the form of a rectangular plate 16, that holds a disk-like filter element 18 behind an opening 17, and an aperture 19 is located in the filter. It is particularly favorable for the aperture holder 3 to consist of two plates 16 positioned to coincide with each other, each of which has an opening 17 so that the disk-like filter unit 18, that consists for example, of cellulose acetate and is coated with collagen, is held between the plates 16. For example, the plates 16, composed of plastic, are glued together or are melted or fused together.

To perform a measurement, the capillary holders 9 and the head part 10 are moved apart so that an aperture holder 3 can be placed onto the surface 9' of the capillary holder 9. Next, the capillary holder 9 and the head part 10 are moved toward each other so that the aperture holder 3 is held between the surfaces 9' and 10' of the capillary holder 9 and the head part 10 facing each other, so that a space 20 of the capillary holder 9 in contact with the capillary 15, and a space 21 of the head part 10 connected with the line 11, are positioned under or over the filter element 18 and are sealed to the side. To effect this seal, as is shown schematically in FIG. 3, a seal 22 surrounding the opening 17 like a ring, can be provided on both sides of the aperture holder 3; the diameter of this seal is greater than the diameter of the space 20 or 21.

After sealing of the test head 7 by pressing of the capillary holder 9 and the head part 10 against the aperture holder 3, the actual measurement can begin, since as was already described, care has been taken that after closure of the test head 7, a supply vessel 5 is present underneath the capillary holder 9 such that the capillary 15 of the capillary holder 9 is immersed into the supply vessel 5.

From FIG. 1 it is evident that the magazine device can be for example, a supply roll 2, from which the aperture holders 3 joined to a tape, can be unrolled. The band-like aperture holders 3 wound up onto the supply coil 2 are very compact, so that they need relatively little space for storage.

But instead of the supply roll 2, the magazine device can have for instance, the form of a hollow, cylindrical magazine 2' in which the single aperture holders 3 are stacked one on top of the other. From this magazine 2' the aperture holders 3 are fed in sequence in the direction of arrow 23 with the aid of known mechanical devices to test station 1 and to the test head 7.

Due to the synchronizing device, also not explained in detail, care is taken that simultaneously one aperture holder 3 is moved from the magazine device 2 or 2' and one supply vessel 5 moves from the magazine 8 to the test head 7.

Now in connection with FIG. 2, one particularly preferred configuration of a test head 7 will be explained in greater detail below. In contrast to the test head described in connection with FIG. 1, the test head 7 of FIG. 2 is intended for aperture holders with several apertures, e.g. with four apertures 19-1, 19-2, 19-3 and 19-4. These apertures should be distributed uniformly along the filter unit 18 held in the aperture holder 3. For example, according to FIG. 4, the four apertures 19-1 to 19-4 are distributed uniformly, spaced from each other by 90°, around a circle at the midpoint of the filter part 18. In order to effect a sealing of the individual apertures from each other, so that with each aperture 19-1 to 19-4 a separate measurement can be carried out, preferably striplike sealing elements 23 and 24 are provided. The sealing elements 23 have the form of a cross dividing the exposed surface of the filter element 18 into four regions, while the sealing element 24 has the form of a circle positioned concentric to the circle on which the apertures 19-1 to 19-4 are located. In each of the formed subsurfaces 18-1 to 18-4 of filter element 18, there is one aperture 19-1 to 19-4 that is isolated from the other apertures. It is also possible to allocate a single, cross-like sealing element to each aperture 19-1 to 19-4, as is illustrated by the dashed line in the example of aperture 19-4 in FIG. 4. In accordance with the distribution of apertures 19-1 to 19-4, in the capillary holder 9 there are recesses 20-1 to 20-4 on the surface facing the aperture holder 3, such that upon contact of the aperture holder 3 onto the surface 9' of the capillary holder 9 facing it, one of the recesses surrounds one aperture. In the illustrated manner, each recess 20-1 to 20-4 is joined with one capillary 15-1 to 15-4. In the manner evident from FIG. 5, that shows a top view of the capillary holder 9 from below, the capillaries 15-1 to 15-4 run from the recesses 20-1 to 20-4 downward so that their neighboring ends can immerse into a supply vessel 5.

In the same manner, recesses 21-1 to 21-4 are provided in the surface 10' of the head part 10 facing the aperture holder 3, of which recesses, each one is surrounded in the closed state of the head part 7 by an aperture 19-1 to 19-4. In this regard we should point out that the sealing elements 23, 24 described above, or the sealing elements illustrated by dashed lines in FIG. 4, are provided on both sides of the aperture holder 3, so that also the recesses 21-1 to 21-4 are sealed against each other. Each of the recesses 21-1 to 21-4 is joined to a line 11-1 to 11-4 that leads to the cylinder 12 mentioned above.

In the described configuration, every capillary 15-1 to 15-4 in conjunction with a recess 20-1 to 20-4, an aperture 19-1 to 19-4, a recess 21-1 to 21-4 and a line 11-1 to 11-4, represents a separate test system. It is expressly pointed out that the filter unit 18 of the aperture holder 3 can have both one, or also several apertures 19 in any number and placement, as long as care is taken that every aperture, in conjunction with the described sealing elements, capillaries and recesses of the capillary holder 9 and the head part 10, can represent a separate measuring system.

When using several measuring systems, different measurements can be taken either with the individual measuring systems, or the same measurements can be carried out with several measuring systems, at least with two measuring systems. In the latter case, the measuring reliability can be increased significantly. To undertake different measurements, the apertures 19-1 to 19-4 can be at least partly of differing size. Before closing the test head 7, that occurs preferably by movement of the head part 10 against the fixed capillary holder 9, on whose surface 9' the aperture holder 3 is positioned, by means of a suitable device, in the direction of the arrow 25, ADP can be input automatically in the single, mutually sealed filter surfaces 18-1 to 18-3, so that the named filter surfaces can be saturated with ADP.

In FIG. 2, the reference numbers 26 and 27 represent a cleaning device, that is used after completion of a measurement, for example to flush the supply vessel 5 to clean it by addition of the rinsing agent via the line 26 from the reservoir 27, whereby thereafter the rinsing agent can be sucked through the capillaries 15-1 to 15-4 to clean the recesses 20-1 to 20-4 and 21-1 to 21-4 and can then be ejected. For this purpose, the lines 11-1 to 11-4 can be disconnected by (not illustrated) valves from the cylinder 12, and can be joined to a pressure source or a vacuum source (also not shown). In addition, in a separate step after removal of a just tested supply vessel, a vessel containing the rinsing agent can be brought into the region of the capillaries.

Notice that in a particularly preferred, cost-effective design in the edge regions of the recesses 20-1 to 20-4 and 21-1 to 21-4, sealing rings 28 are held in such a manner that the isolation of the single recesses and apertures from each other takes place upon closure of the test heads, since the seals 28 are pressed against the filter unit 18, whereby one sealing ring 28 surrounds one aperture 19-1 to 19-4. In this case, the aperture holders 3 need not exhibit the mentioned sealing elements 23 and 24, so that they are particularly low in cost to produce.

Figure 6:
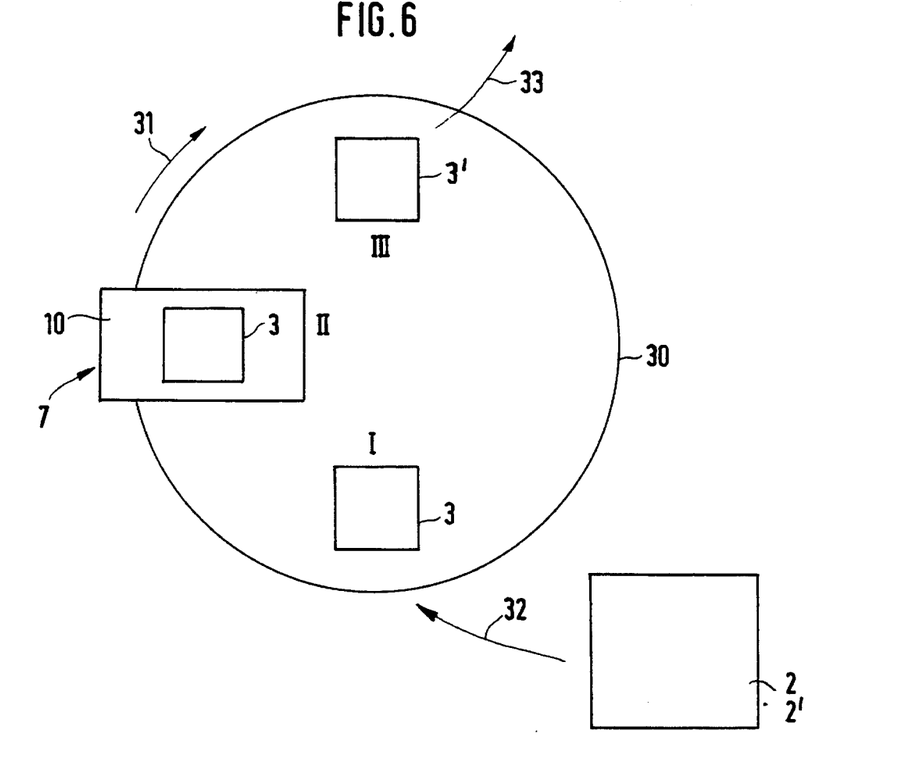
FIGS. 6 and 7 show transport features for aperture holders.
Figure 7:
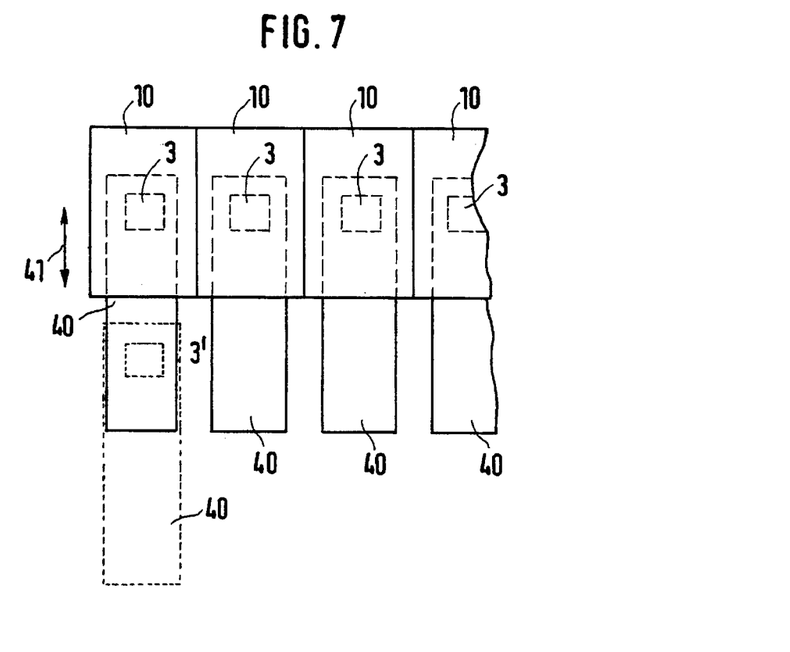

With reference to FIGS. 6 and 7, exemplary, particularly preferred features will be explained below, with whose assistance sequential test operations can be carried out, whereby at the same time with one test operation, after removal of one aperture holder, a rinsing operation can be carried out.

FIG. 6 shows a transport disk 30 that is being fed in a first position at time $t_1$, an aperture holder 3 from a magazine device 2 or 2', along the path 32 at a site I. Now the aperture holder 3 is positioned in a specified position along the transport disk 30. At a distance from the site I there is a test head 7 at site II, where at time $t_1$ of the arming of the site I, with an aperture holder 3, one measurement will be carried out at another aperture holder 3. At the site III there is at this time an already tested aperture holder 3', that at this time is taken off from the path 33 of the transport disk 30.

At time $t_2$ the transport disk 30 will be turned in the rotary direction 31 in such a manner that the aperture holder located at site I moves to a site between the sites I and II and that the aperture holder at the site II is turned from the test head 7 at a site between the sites II and III. While the transport disk 30 remains in this setting, the test head 7 will be closed and a rinsing operation will be carried out in the manner explained in connection with FIG. 2.

At the end of the rinsing operation, the test head 7 will be opened again and at the time $t_3$, the transport disk 30 will be turned in the direction 31 such that the aperture holder 3 located between the sites I and II moves into the test head 7, and the aperture holder 3' located between the sites II and III moves to the site III where a measurement was already carried out. The test head 7 will then be reclosed, and a new measurement will be carried out. At the same time, at site I, a new aperture holder 3 from the magazine device 2, 2', will again be fed in, while from site III, the aperture holder 3' will be removed.

In the illustrated manner, the sites I, II and III are located at a distance from each other on the transport disk 30, for example, by 90°.

From FIG. 7 we see a refinement of the present device, where the aperture holders 3 are positioned on a slide 40, that in its one position (upper illustration of FIG. 7) is pushed into the opened test head 10 together with the aperture holder and that in its other position (dashed illustration of FIG. 7) is pushed out from the test head 10. In this other setting, the test head 10 will be closed and cleaned in the manner already described. At the same time, the aperture holder 3, on which a measurement had just been completed, is removed from the slide 40 and from the magazine device 2 or 2' a new aperture holder 3 is applied to the slide 40.

The sample design of FIG. 7 is particularly advantageous, because, as is evident, to save space, the preferably rectangular shaped test heads 10 can be positioned directly side by side.

In the designs of FIGS. 6 and 7, the supply vessels can also be fed in by means of another transport disk or by another slide, whereby the movements of the other transport slides or of the other slide and the movements of the transport slide 30 or of the slide 40, for instance, can be synchronized by mechanical features.

It is expressly pointed out that the schematic representation of FIG. 2 is to be understood such that a separate cylinder 12 is connected to every line 11-1 to 11-4 etc., in which one piston 13 is located.

Figures 8, 9, 10, 11, 12:
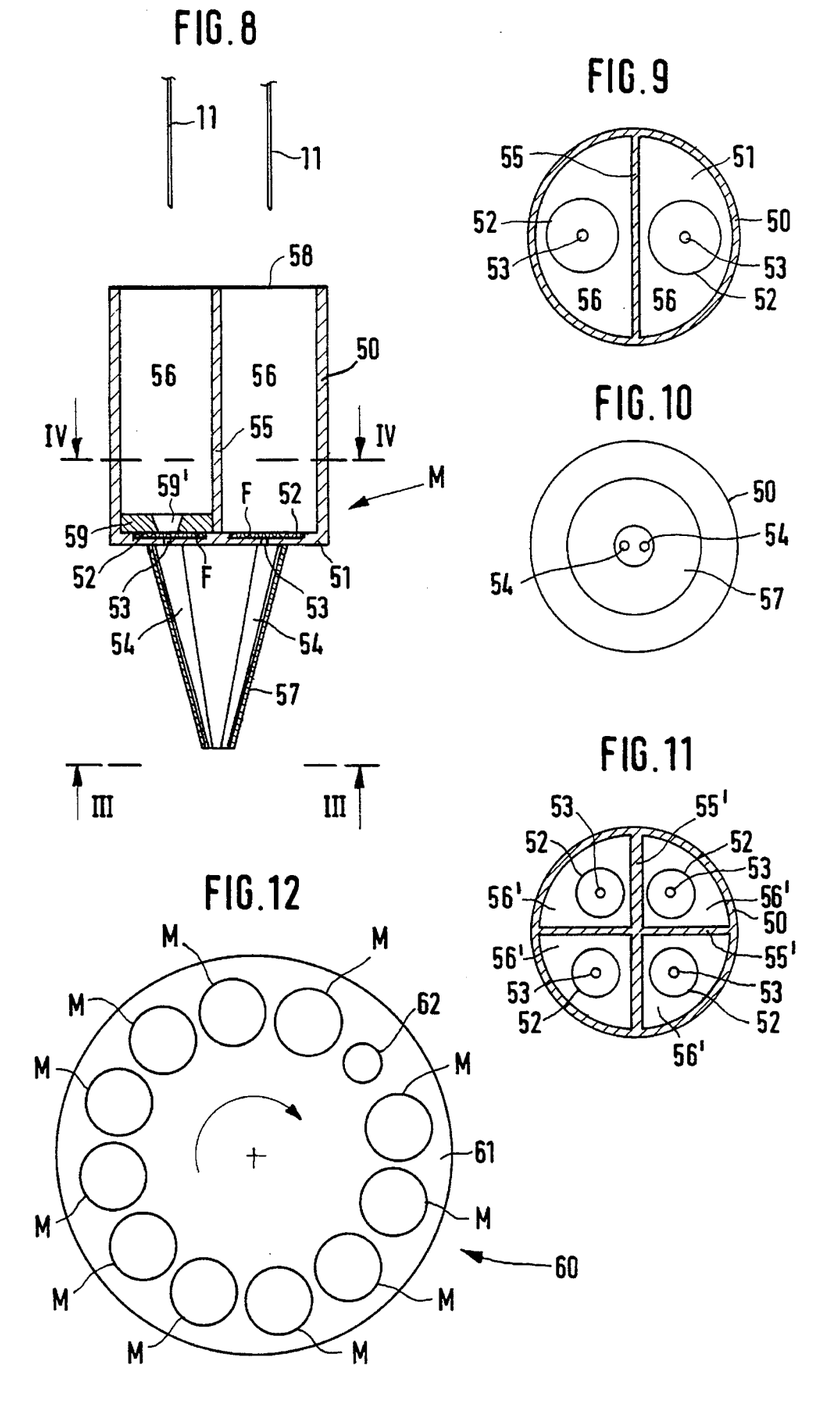
FIGS. 8, 9, 10, and 11 show a disposable measuring units, with several capillaries, blood sampling areas and filter units.
FIG. 12 shows a magazine device, e.g. for measuring units as per FIGS. 8 to 11.

A measuring unit M will be explained below in connection with FIGS. 8 to 11; this measuring unit contains preferably two or more capillaries 6, one holding vessel 1 for blood and several filter parts F corresponding to the number of capillaries 6 (FIG. 8). Now the measuring units M are disposable items that are fed preferably to test station 1 from a magazine device. Every measuring unit M has one blood sampling container 50, which is preferably a cylindrical vessel with a base unit 51. At the inside of the base unit 51 there are preferably recesses 52 into which filter elements F can be inserted in such a manner that their apertures (not illustrated) are directed toward openings 53 located in the base wall. At the side of the base wall 51 turned away from the filter parts F, capillaries 54 are set onto these filter elements so that the inner openings of the capillaries 54 open directly or indirectly into the openings 53. The capillaries 54 are connected preferably on a slant to the base part 51 in such a manner that they run to a site at a distance from the base wall 51 to form an acute angle.

Care has been taken that the filter parts F are employed in the recesses 52 in such a manner that blood sucked in through the capillaries 54, passes through the opening 53 and the apertures of the filter elements F located behind them, and can not flow along the base of the recesses 52 while bypassing the apertures of the filter elements F.

In the interior of the container 50 there is a separator wall 55 that divides the container 50 into preferably two chambers 56, whereby to each chamber 56, a separate filter section F and perhaps one locking clip 59 is allocated. In the case of a cylindrical container 50, the separator wall 55 runs preferably in such a manner that the vessel 50 is divided into two parts of equal size. The separator wall runs at the side of the container 50 turned away from the base unit 51 out to the level of the container wall.

As is illustrated in FIG. 8 for the left chamber, a locking clip 59 with filling funnel 59', can be inlet-connected to the filter unit F, in such a manner that the filling funnel is inlet-connected to one of the apertures of the filter unit F. In the filling funnel 59', liquid substances can be poured in, e.g. to influence the primary blood coagulation. The locking clip 59 can be attached or snapped into the proper position, preferably with the aid of locking features (not illustrated).

The capillaries 54 are surrounded preferably by a housing section 57 that is set onto the base part 51 and that has the form of a cone running at a point to the named site. The purpose of this housing part consists in the fact that the capillaries 54 are lined for optical reasons, and protected against shocks or damage. In addition, the free end of the housing section 57 forms a defined peak, with whose assistance it is possible to penetrate the seal of a blood vessel.

The housing part 57 can also have the form of a massive block in which the capillaries 54 are formed as through-holes or leads.

At the side turned away from the capillaries 54, the container 50 is sealed by a sealing device 58, that is preferably an adhesion seal or an elastic membrane, for example, a rubber membrane or similar item. In this sealing device 58 it is possible to insert the pointed ends of lines 11 running to the cylinders described in detail above, in order to generate a vacuum for the intake of blood through the capillaries 54 from a supply vessel into the holding chambers 56. After the implementation of a measuring operation, the lines 11 will be pulled out of the sealing device 58, whereby care is taken that the openings of the sealing devices 58 close back again so that no blood can flow out of the holding chambers 56.

In the manner evident from FIG. 11, the described measuring unit M can also be divided into more than two, for example into four, holder chambers 56' by separating walls 55', whereby the four capillaries then present, are likewise surrounded by a housing part in the manner illustrated in conjunction with FIG. 8 and that run to a pointed site.

The advantage of the described measuring unit M designed as a disposable unit, consists in the fact that they make the elements 15, 9, 3 and 10 of FIG. 2 dispensable. Or expressed differently, the use of the measuring units M leads to a significant reduction in expense of the present device for automatic investigation of blood samples. An additional reduction in expense is obtained since the operation of this device is made much simpler. Due to the provision of several filter parts F, several capillaries 54 and several blood sampling areas 56, several measurements can be performed with one and the same measuring unit at one sealing site, which is why at any particular operating time of the device, many more measurements can be conducted.

When making the division into several channels or holding chambers by use of separating walls 55, 55', for example for safety reasons parallel measurements can be performed, and if they coincide it is assured that no errors were present. In addition, single or even parallel measurements can be undertaken with different inductors. For example, in the configuration of FIG. 11, measurements can be carried out with four inductors, e.g. with ADP, calcium chloride, adrenaline and ristocetin in one measuring operation at the same time. Thus simultaneously, different information can be obtained from one and the same blood sample by means of the primary coagulation. Likewise, filter parts can also be used that differentiate with respect to the aperture parameters and quantity, and also e.g. the type of collagen coatings. Furthermore, differentiated information can also be obtained in this manner.

In accordance with FIG. 12, the measuring units described above will be moved preferably by a magazine device 60 into the test station that has the form of a carousel-like device. More accurately, the individual measuring devices M are located on a disk or similar item that is turned in steps into the region of the test station. For example, this disk 61 has holes 62 in which the housing parts 57 of the measuring units M are inserted, so that the measuring units M rest on the surface of the disk 61 with the edge regions of the base unit 51 surrounding the housing parts 57. Notice that as magazine device, other features are also suitable in which the measuring units M are stacked or are coiled up like a band or tape. These features were already explained in conjunction with FIG. 1. Likewise, it is also possible to feed the aperture holders 3 and/or the supply vessels 5 from a carousel-like magazine device.

Figure 13:
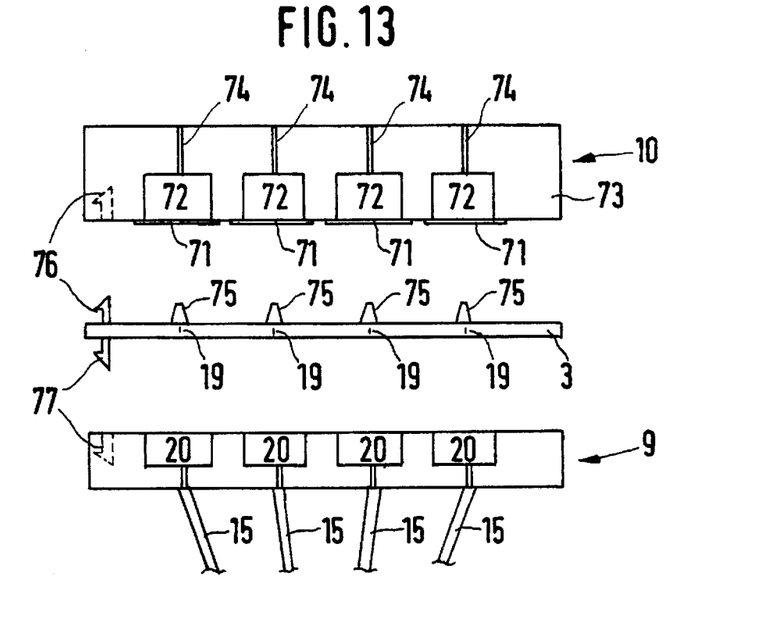
FIG. 13 shows a head unit designed as a disposable article.

FIG. 13 shows a design of the head unit 10 as a disposable item. There are recesses 72 placed in a unit or disk-like part 73 separated from each other to form the blood holding chambers. These recesses open up on the one side of the part 73 that is facing the aperture holder 3 in the test head 7 (FIG. 2). At this side the recesses 72 are sealed by membrane elements 71, e.g. made of a rubber material or of soft plastic, that will open automatically when closing the test head. For this purpose, the membrane elements 71 have e.g. weak places and conical hollow peaks 75 penetrate into them when closing the test head; these peaks are inlet-connected to the apertures 19 of the aperture holder 3 such that in the measuring process, blood sucked through the apertures 19 moves through the hollow peaks 75 and the perforated membrane elements 71 into the recesses 72. Channels 74 open into the recesses 72 preferably from the side turned away from the aperture holder 3, whereby these channels 74 open toward one outer side, preferably to the side of the part 73 opposite the membrane elements 71. When closing the test head, the ends of the lines 11 will be automatically and tightly connected to the channels 74.

It is expressly pointed out that the membrane elements 71 can also be used simultaneously to provide the seal between a filter part 18 held in the aperture holder 3, and the corresponding blood sampling chamber formed by a recess 72.

After completion of a measurement and opening of the test head, the hollow peaks 75 are pulled out from the membrane elements 71, whereby the membrane elements 71 close up again, so that no blood can exit from the recesses 72. The head parts 10 designed as disposable units can then be discarded.

It is also possible to design the disposal of the aperture holders 3 together with the head parts 10, as shown in FIG. 13, left, when closing the head part 10 if the aperture holder 3 is automatically locked to part 73 by using the locking features 76. For example, this type of locking feature 76 has a locking hub at the aperture holder 3 or at part 73, that snaps into a corresponding recess at the part 73 or at the aperture holder when the test head is closed.

The part 73 consists preferably of polystyrene or PVC.

Since the head part 10 is designed as a disposable unit, the rinsing processes explained in conjunction with FIG. 2 for the head part 10 are not needed.

It is also possible to design the capillary holder 9 (FIG. 2) as a disposable unit, where in this case, the recesses 20 of the capillary holder 9 need not be sealed by membrane elements, since no blood can exit from them. As is illustrated in FIG. 13, in a case when both the head part 10 and also the capillary holder 9 are designed as disposable parts, even if a locking mechanism 77 is provided between the aperture holder 3 and the capillary holder 9, a common disposal of the head part 10, of the aperture holder 3 and of the capillary holder 9 can be undertaken.

When designing the capillary holder 9 as a disposable part, the rinsing processes described in connection with FIG. 2 for this part are also unnecessary.

Figure 14:
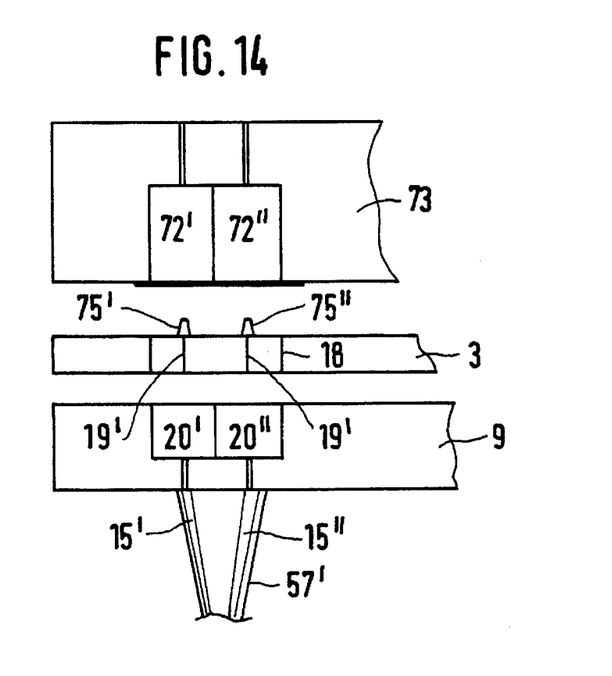
FIG. 14 shows another design of the head unit.

It is expressly pointed out that as explained in regard to FIGS. 8 to 11, even in the designs of FIG. 13, every recess 72 of the head part 10 can be divided by corresponding separating walls that correspond to the separating walls 55 or 55' of FIGS. 8 or 11, into several, for example, two or four, blood sampling chambers 72', 72". In this case, every recess 72 has been allocated a corresponding filter unit held by the aperture holder 3, that has at least one aperture 19 and perhaps also a hollow peak 75 inlet connected to it, for every blood sampling chamber 72', 72". Accordingly, every recess 20 of the capillary holder 9 is divided into several smaller chambers 20', 20", whereby every partial chamber 20', 20" is allocated to one blood sampling chamber of the head part 10 and to one capillary 19 with a specified, preset hollow peak 75 of one filter part 18 of the aperture holder 3. Every partial chamber is also connected to its own capillary, whereby the capillaries of the partial chambers of one recess are surrounded by a housing part. This is shown schematically in FIG. 14 for the provision of two blood sampling chambers per recess 72, two apertures 19 per filter unit 18, and two partial chambers 20 per recess 20.

Notice also that the described measuring unit, that makes it possible to dispense with the rinsing processes at the test head, is not limited to uses in the explained device for automatic examination of blood samples.

It is also possible to divide the supply vessel by at least one separating wall 5" (see FIG. 1) into several partial chambers, where one capillary 15 for blood sampling is allocated to each partial chamber.

The "filter unit" means a part that consists of a porous unit (e.g. a filter part or collagen itself) or a membrane and that is braced by an impermeable material. One or more apertures can be located in the porous part.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A device for the automatic examination of blood samples, said device comprising:

a test station;

a plurality of aperture holders each defining a preformed aperture which extends through said aperture holder and which simulates an injured portion of an arteriole;

first magazine holder means for conveying a plurality of supply vessels filled with blood into a position for communication with said test station;

second magazine holder means for conveying said plurality of aperture holders to test station;

test head means provided at said test station for drawing blood from said supply vessels through said preformed apertures in said aperture holders and for taking a measurement of blood flow through each of said apertures;

discarding means for removing said aperture holders and supply vessels from said test head means after said test head means has taken said measurement; and cleaning means for circulating a rinsing agent through said test head means.

2. The device of claim 1 in which each of said aperture holders comprises a plate member defining an opening with a filter layer being positioned across said opening, said filter layer defining said aperture.

3. The device of claim 2 in which said filter layer comprises a layer of cellulose acetate coated with collagen.

4. The device of claim 2 in which said plate member comprises first and second halves defining coincident holes that form said opening, said filter layer being interposed between said first and second halves and extending across said opening.

5. The device of claim 1 in which said second magazine holder means comprises a housing containing a supply coil formed from said plurality of aperture holders which are formed together in a continuous band and rolled into said supply coil.

6. The device of claim 1 in which said second magazine holder means comprises an elongate housing containing said plurality of aperture holders which are unconnected and stacked one on top of another.

7. The device of claim 1 in which said test head means comprises a capillary holder having at least one capillary positioned to be insertable into one of said supply vessels and a head part positioned adjacent said capillary holder; one of said capillary holder and said head part being moveable so that said capillary holder and said head part may be moved from a first position in which they are spaced apart for receiving one of said aperture holders therebetween and a second position in which said one of said aperture holders is clamped between said capillary holder and said head part.

8. The device of claim 7 in which said capillary holder has a mating surface adjacent said head part; said mating surface including a recess in communication with said at least one capillary and positioned to surround said aperture when said one of said aperture holders is clamped between said capillary holder and said head part.

9. The device of claim 8 in which said head part includes a mating surface adjacent said capillary holder; said mating surface including a recess in communication with a vacuum means and being positioned to surround said aperture when said one of said aperture holders is clamped between said head part and said capillary holder.

10. The device of claim 9 in which said recess of said capillary holder and said recess of said head part are coincident.

11. The device of claim 9 in which each of said plurality of aperture holders includes a pair of ring-shaped sealing rings each respectively surrounding a top and bottom of said aperture and positioned to sealably mate with said recesses and said capillary holder and said head part.

12. The device of claim 9 in which said recesses of said capillary holder and said head part each have ring-shaped sealing elements provided about their periphery and positioned to surround said aperture when said one of said aperture holders is clamped between said capillary holder and said head part.

13. The device of claim 7 in which each of said aperture holders defines a plurality of said apertures; said capillary holder and said head part each including an adjacent mating surface; each of said mating surfaces respectively having a plurality of pairs of coincident recesses; each of said pairs of recesses being positioned to surround one of said plurality of apertures in said aperture holder when said aperture holder is clamped between said head part and said capillary holder.

14. The device of claim 7 in which said cleaning means is positioned to input a rinsing agent into said supply vessel so that said cleaning agent can be circulated through said capillary, said capillary holder and said head part.

15. The device of claim 1 in which insertion means is provided for receiving said plurality of said aperture holders from said second magazine holder means and inserting and retracting said aperture holders into and out of said test head means.

16. The device of claim 15 in which said device includes a plurality of said test head means positioned adjacent to each other.

17. The device of claim 1 in which rotary disc means are provided for feeding said plurality of aperture holders through said test head means by rotating a rotary disc from a first position in which said rotary disc receives said aperture holder, a second position in which said aperture holder is positioned in said test head, and a third position in which said aperture holder is positioned for removal from said rotary disc.

18. The device of claim 7 further comprising carrousel magazine means for bringing a plurality of said capillary holders into said test head means in a step wise fashion.

19. The device of claim 18 in which said carrousel magazine means includes a carrousel disc having a plurality of holes adapted to receive said plurality of capillary holders.

20. The device of claim 7 in which said head part comprises a disposable housing having a plurality of recesses on a mating surface adjacent said capillary holder; each of said recesses defining an opening sealed by a membrane; said device including opening means for automatically opening said membranes when said head part and said capillary holder are clamped together.

21. The device of claim 20 in which said disposable housing is disc-shaped and includes a plurality of channels each in communication with one of said recesses at one end and in communication with vacuum means at the other end.

22. The device of claim 20 in which each of said plurality of aperture holders has a hollow peak member extending in a perpendicular direction from each of said aperture holders and is positioned to surround said aperture; said hollow peak members being positioned to penetrate said membranes covering said recesses of said disposable housing when said head part and said capillary holder are clamped together.

23. The device of claim 22 in which said disposable housing and each of said aperture holders are provided with locking means for locking said disposable housing and said aperture holders together when said test head and said capillary holder are clamped together.

24. The device of claim 20 in which said capillary holder comprises a disposable unit having a plurality of recesses on a mating surface adjacent said head part; said disposable unit including a plurality of channels which respectively connecting said plurality of recesses to a plurality of said capillaries.

25. The device of claim 24 in which said capillary holder further includes locking means for locking said capillary holder to said plurality of said aperture holders when said capillary holder and said head part are clamped together.

26. The device of claim 13 in which said pairs of said recesses of said head part and said capillary holder include a plurality of separating walls to divide each of said pair of said recesses into a plurality of chambers, each of said chambers being positioned to surround one of said apertures in said capillary holder.

27. The device of claim 7 in which said head part and said capillary holder are comprised of one of polystyrene and PVC.

28. The device of claim 1 in which said plurality of aperture holders are comprised of polystyrene and PVC.

29. The device of claim 1 in which each of said supply vessels is divided by at least one separator wall into a plurality of vessel chambers.

* * * * *